United States Patent [19]

Adkins

[11] Patent Number: 5,046,301
[45] Date of Patent: Sep. 10, 1991

[54] ASBESTOS BULK EXTRACTOR AND METHOD THEREFOR

[76] Inventor: Wayman L. Adkins, 17549B Ashbourne La., Boca Raton, Fla. 33496

[21] Appl. No.: 462,043

[22] Filed: Jan. 8, 1990

[51] Int. Cl.$^5$ ............................................. B65B 63/00
[52] U.S. Cl. ...................................... 53/435; 53/520; 408/68; 73/864.44
[58] Field of Search ...................... 83/919; 408/67, 68, 408/58; 73/864.44, 864.45, 864.34; 175/308, 313, 20, 209, 211, 213, 214; 53/435, 520, 521

[56] References Cited

U.S. PATENT DOCUMENTS

| | | | |
|---|---|---|---|
| 983,810 | 2/1911 | Crossley | 408/68 |
| 1,705,049 | 3/1929 | Fournier | 408/68 |
| 2,327,497 | 8/1943 | Burch et al. | 175/208 |
| 4,652,184 | 3/1987 | Fischer | 408/67 |
| 4,754,655 | 7/1988 | Parker, III | 73/864.44 |
| 4,887,413 | 12/1989 | Tuckey, Jr. | 408/68 X |

Primary Examiner—Larry I. Schwartz
Assistant Examiner—Robert Schultz
Attorney, Agent, or Firm—Robert C. Kain, Jr.

[57] ABSTRACT

The asbestos bulk extractor includes, in a preferred embodiment, an elongated housing having a handle section normal thereto. The housing defines an interior chamber and the handle defines a through port between the chamber and a vacuum line. At one end of the housing, a transparent, rigid hood is removably attached which defines an extraction region. A coring tube is rotatably and longitudinally retained within the housing and extends beyond both ends of the housing. The coring tube has a coring end which bores into the asbestos containing material. The other end of the coring tube is manually operable such that the tube can be rotated and forced into the asbestos containing material. An extraction push piece is movably mounted within the coring tube. After the coring tube has bored into the asbestos containing material, the coring tube is withdrawn from the extraction site and the core sample held within the coring end of the tube is pushed from the tube by the push piece into a vial. During the coring operation, the hood is placed on the surface of the asbestos containing material and, since the interior region of the hood is in communication with the housing chamber and the output port, the hood is maintained at a negative pressure during the boring operation, the withdrawal of the sample and when the hood is placed over the vial to contain the sample, the vial itself is in a region of negative pressure. A method is also disclosed.

21 Claims, 1 Drawing Sheet

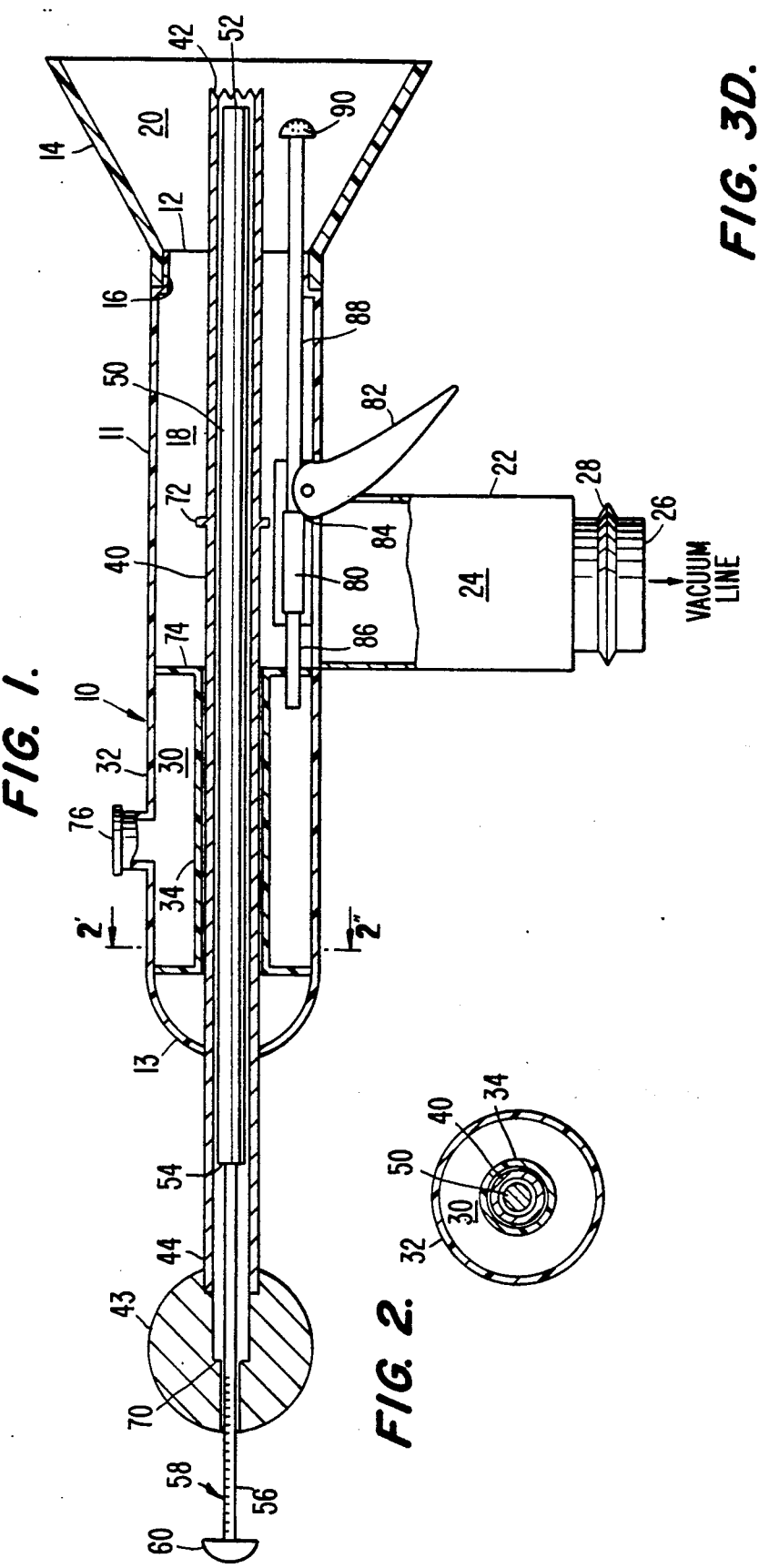

ASBESTOS BULK EXTRACTOR AND METHOD THEREFOR

BACKGROUND OF THE INVENTION

The present invention relates to an asbestos bulk extractor, that is, a device for obtaining a bulk sample of asbestos containing material, and a method for extracting or obtaining that sample.

One prior art device, a Nilfisk asbestos bulk sampler, manufactured by Nilfisk of America, Inc. of Malvern, Pa., utilizes a flexible, cone shape hood which defines an extraction region about an extraction site. A fixed corer is mounted in the interior of the flexible cone. The cone and fixed corer are mounted on the end of a vacuum hose. The operator places the cone/corer over the extraction site and moves the cone, corer and vacuum hose back and forth to core and obtain a sample of the material potentially containing asbestos. To remove the asbestos containing material, the operator detaches the corer base from a cylindrical holder in the interior of the flexible cone and withdraws the sample and places it in a vial or container.

OBJECTS OF THE INVENTION

It is an object of the present invention to provide an asbestos bulk extractor which cores a sample of the asbestos containing material, withdraws that sample, and then is capable of depositing the sample into a container while substantially simultaneously maintaining a negative pressure under an extraction hood.

It is another object of the present invention to provide an asbestos bulk extractor that is manually operated and which permits the operator to view the coring operation.

It is a further object of the present invention to provide an asbestos bulk extractor that wets the extraction site immediately after the sample is withdrawn.

It is another object of the present invention to provide an asbestos bulk extractor that provides an indication to the operator of the depth of the core.

SUMMARY OF THE INVENTION

The asbestos bulk extractor includes, in a preferred embodiment, an elongated housing having a handle section normal thereto. The housing defines an interior chamber and the handle defines a through port between the chamber and a vacuum line. At one end of the housing, a transparent, rigid hood is removably attached which defines an extraction region. A coring tube is rotatably and longitudinally retained within the housing and extends beyond both ends of the housing. The coring tube has a coring end which bores into the asbestos containing material. The other end of the coring tube is manually operable such that the tube can be rotated and forced into the asbestos containing material. An extraction push piece is movably mounted within the coring tube. After the coring tube has bored into the asbestos containing material, the coring tube is withdrawn from the extraction site and the core sample held within the coring end of the tube is pushed from the tube by the push piece into a vial. During the coring operation, the hood is placed on the surface of the asbestos containing material and, since the interior region of the hood is in communication with the housing chamber and the output port, the hood is maintained at a negative pressure during the boring operation, the withdrawal of the sample and when the hood is placed over the vial to contain the sample, the vial itself is in a region of negative pressure. A method is also disclosed.

BRIEF DESCRIPTION OF DRAWINGS

Further objects and advantages of the present invention can be found in the detailed description of the preferred embodiment when taken in conjunction with the accompanying drawings in which:

FIG. 1 schematically illustrates the asbestos bulk extractor;

FIG. 2 is a cross-sectional view of the extractor from the perspective of section line 2'—2" in FIG. 1; and FIGS. 3A, 3B, 3C and 3D illustrate the operation of the extractor.

DETAILED DESCRIPTION OF THE PREFERRED EMBODIMENT

The present invention relates to an asbestos bulk extractor and a method for obtaining samples of asbestos containing materials.

FIG. 1 schematically illustrates asbestos bulk extractor 10. Housing 11, preferably made of plastic, has a first end 12 at which is removably mounted a transparent, rigid hood 14. Hood 14 is mounted on housing 11 by an interference fit in step region 16. Housing 11 defines, in its interior, a chamber 18. End 12 is essentially open to extraction region 20 defined within the interior of hood 14. In the preferred embodiment, housing 11 is an elongated cylinder to which is attached a handle section 22. The interior portion 24 of handle 22 is hollow and end 26 defines a port to a vacuum line. Preferably, the vacuum line is attached to the input port of a high efficiency, particle absolute vacuum system which is specially designed for capturing asbestos particles. Ridges 28 on the housing remote end of handle 22 are adapted to coact with and hold the vacuum hose line on the handle. Therefore, extraction region 20 within the interior of hood 14, housing chamber 18, and handle chamber 24 communicate with the interior of the vacuum line and are placed under a negative pressure when the vacuum is activated. As used herein, the term "negative pressure" refers to a pressure at least less than the ambient atmospheric pressure and, preferably, much lower than the ambient pressure such that any friable asbestos particles released during the coring or removal steps are carried by the negative pressure into the high efficiency, particle absolute vacuum system.

Housing 11 also contains a fluid chamber 30 that is defined in part by housing outer wall section 32 and an inboard cylindrical wall 34.

FIG. 2 illustrates a cross-section of the extractor from the perspective of section line 2'—2". Housing wall 32 provides the circumferentially outer wall of fluid chamber 30 and inboard cylindrical wall 34 provides the radially inboard containment wall of that chamber.

Returning to FIG. 1, a coring tube 40 extends beyond opposing ends 12 and 13 of housing 11. The coring tube has a coring end 42 that is movable throughout extraction region 20. Coring end 42 defines boring teeth capable of sawing the asbestos containing material when the tube is rotated. Coring tube 40 is rotatably and longitudinally held within housing 11 by inboard cylindrical wall 34 which defines a sleeve about tube 40. See FIG. 2. A ball handle 43 is attached to the extraction remote end 44 of tube 40. Handle 43 is a means for rotatably and longitudinally moving the tube and the coring end through the extraction region and into an extraction site.

In the interior of coring tube 40, a push rod or piece 50 is disposed. Push piece 50 is longitudinally movable within coring rod 40. End 52 of push piece 50 is flat to enable the core sample to be ejected from coring tube 40. Push piece 50 has a step 54 and a smaller diameter section 56 that extends through ball handle 43. Indicia at end region 58 of extension section 56 provides the operator with an indication of the depth coring tube 40 has entered into the asbestos containing material. Knob 60 at the end of push piece 50 limits the outboard movement of push piece 50 beyond coring end 42 of coring tube 40. Step 54 limits the outboard movement of push piece 50 away from coring end 42 by its coaction with step 70 in the interior of ball handle 43.

As shown in FIG. 2, push piece 50 is loosely retained within coring rod 40. Preferably, coring rod 40 is metal, as is push piece 50. Movement of coring end 42 and hence coring tube 40 toward the extraction site is limited by ball handle 43 coacting with remote housing end 13. Movement of coring rod 40 away from the extraction site is limited by stop 72 coacting with radially disposed side wall 74 of fluid chamber 30.

Fluid chamber 30 is sealed by removable cap 76. The fluid in chamber 30 is a surfactant that wets the extraction site after withdrawal of the sample core from the asbestos containing material. The surfactant fluid from chamber 30 is sprayed onto the extraction site by a pump 80 that is actuated by pump trigger 82. Linkage 84 mechanically couples trigger 82 to pump 80. A fluid delivery system for the wetting agent includes a supply line 86 fluidly coupled to the interior of chamber 30 and a fluid output line 88 coupled to the output of pump 80. A spray head 90 is disposed at the end of fluid line 88 in the interior of hood 14 that defines extraction region 20.

Essentially, coring tube 40 is rotatably and longitudinally held within the sleeve defined by inboard cylindrical wall 34. The tube, as well as the push rod 50, can be moved longitudinally within the housing. The right hand portion of the tube between stop 72 and coring end 42 is essentially free-standing, as is fluid output line 88 and spray head 90. In this manner, friable material generated during the coring operation is suctioned by the vacuum line from extraction region 20, through housing chamber 18, handle chamber 24 and into the vacuum system.

FIGS. 3A, 3B, 3C and 3D illustrate the major steps involved in the method of extracting the asbestos bulk sample. FIG. 3A shows rigid hood 14 placed adjacent surface 110 of the asbestos containing material. Coring end 42 is manually maneuvered toward extraction site 112 by pushing ball handle 43 toward the site. In FIG. 3A, end 52 of push rod 50 has not yet been placed adjacent extraction site 112. In FIG. 3B, push piece 52 has been placed atop extraction site 112 and coring end 42 has been rotated and pushed below surface 110 such that a core has been cut from the asbestos containing material. Friable particulate 114 is graphically illustrated as being released due to the coring operation. This friable material is sucked from extraction region 20 in the direction of arrow 116 by the vacuum system which has been activated.

In FIG. 3C, an asbestos bulk sample 120 has been withdrawn from extraction site 112 thereby leaving a cylindrical, partial bore 118 in surface 110. The surfactant fluid is sprayed from spray head 90 and is graphically illustrated as particulate spray 122. The surfactant spray step is very important because without the spray, the friable material from the asbestos containing material may enter and pollute the atmosphere. The surfactant spray wets surface 110 of the asbestos containing material as well partial bore 118, thereby significantly reducing, if not eliminating, the friable material. The entire procedure of boring, withdrawing the core sample and spraying is all done under negative pressure since the vacuum line is continually suctioning the friable material and atmosphere away from the extraction site. After hood 14 is removed from the extraction site, the operator seals the site with tape or other suitable cover.

FIG. 3D illustrates the step of depositing sample core 120 into a vial or container 140. Push rod end 52 is longitudinally moved toward coring end 42 of the coring tube thereby ejecting asbestos sample 120 into container 140. Again, the vacuum system is operable and a negative pressure is established in extraction region 20 during the ejection of core sample 120 into container 140. This feature of the invention is important in that the friable material from core sample 120 does not enter the atmosphere due to the negative pressure established within extraction region 20. Further, the operator need not handle core sample 120 thereby limiting exposure of the operator to asbestos particulate.

The claims appended hereto are meant to cover modifications and changes within the spirit and scope of the present invention. For example, housing 11 need not be elongated but can be differently shaped. Coring tube 40 need not extend through the entire housing. Ball handle 43 can be connected to coring tube 40 through a gear and pinion such that the handle is normal to the longitudinal extent of the coring tube 40. That is, the means for rotating and longitudinally moving the coring tube can be changed to extend above and beyond the housing through a slot. Coring heads can be removably attached to coring end 42 of tube 40 such that different heads can be used to bore into different materials. The loose fit between the sleeve defined by inboard wall 43 as well as the loose fit between push rod 50 and coring tube 40 permits the asbestos particulate material to be suctioned by the vacuum line. In other words, air flow from both ends of the housing into the vacuum line is permitted. The extraction region defined by the hood can be placed under negative pressure by means other than the internal housing chamber, such as a direct connect vacuum line to the hood. Hood 14 is removably attached to housing 11 in order to facilitate the cleaning of the interior portions of the housing. Hood 14 is transparent and hence the operator can visually ascertain the effectiveness of the coring step as well as the amount and degree of friable material released during the boring or coring step. Fluid chamber 30 can be relocated into the handle section. In that event, some type of sleeve or support system, such as a pair of retention rings, could be positioned within the housing at a proper location such that coring tube 40 is longitudinally and rotatably held within the housing. Also, the longitudinal movement of push rod can be accomplished by different mechanisms, such as a right angled push bar handle extending through a slot normal to the longitudinal extent of coring tube 40. These features are meant to be encompassed by the appended claims.

What is claimed is:

1. An asbestos bulk extractor operatively coupled to a vacuum source comprising:

a housing having at one end thereof a hood defining an extraction region, means for establishing communication between said vacuum source and said extraction region such that during operation a negative pressure is maintained in the extraction region;

a coring tube having a coring end, means for movably mounting said coring tube in said housing and for extending said coring end from within said housing through said extraction region and into an extraction site in said extraction region;

an extraction push piece movably mounted within said coring tube and means for longitudinally moving said push piece through said coring tube such that an asbestos bulk sample obtained from said extraction site can be ejected from said coring tube; and means for controllably emitting a wetting solution into said extraction region while said region is under negative pressure.

2. A bulk extractor as claimed in claim 1 wherein said coring tube is rotatably retained in said housing and said means for mounting and extending said tube includes means for rotatably and longitudinally moving said coring tube.

3. An asbestos bulk extractor operatively coupled to a vacuum source comprising:

a housing having at one end thereof a hood defining an extraction region, said housing having a through port that provides communication between said vacuum source and said extraction region such that during operation a negative pressure is maintained in the extraction region;

a coring tube having a coring end, means for movably mounting said coring tube in said housing and for extending and rotating said coring end from within said housing through said extraction region and into an extraction site in said extraction region;

an extraction push piece movably mounted within said coring tube and means for longitudinally moving said push piece through said coring tube such that an asbestos bulk sample obtained from said extraction site can be ejected from said coring tube; and, means for controllably emitting a wetting solution into said extraction region while said region is under negative pressure.

4. A bulk extractor as claimed in claim 3 wherein said means for movably mounting said tube includes means for rotatably and longitudinally moving said coring tube with respect to said housing.

5. An asbestos bulk extractor operatively coupled to a vacuum source comprising:

a housing having at one end thereof a hood defining an extraction region, said housing having a through port that provides communication between said vacuum source and said extraction region such that during operation a negative pressure is maintained in the extraction region;

a coring tube having a coring end, means for movably mounting, both rotatably and longitudinally, said coring tube in said housing and for extending and rotating said coring end from within said housing through said extraction region and into an extraction site in said extraction region;

an extraction push piece movably mounted within said coring tube and means for longitudinally moving said push piece through said coring tube such that an asbestos bulk sample obtained from said extraction site can be ejected from said coring tube; and, means for controllably emitting a wetting solution into said extraction region while said region is under negative pressure.

6. A bulk extractor as claimed in claim 5 wherein said means for movably mounting, extending and rotating said coring tube extends beyond said housing away from said one end and is manually operably.

7. A bulk extractor as claimed in claim 6 wherein said means for longitudinally moving said push piece extends beyond said housing and is manually operable.

8. A bulk extractor as claimed in claim 5 wherein said through port is a chamber within said housing and includes an output port that is operably coupled to said vacuum source, said coring tube extending through said chamber and into said extraction region.

9. A bulk extractor as claimed in claim 8 wherein said means for emitting said wetting solution includes a fluid chamber retained within said housing, a pump and a fluid delivery system coupled to said fluid chamber and said pump, said fluid delivery system including a spray head disposed in said extraction region.

10. A bulk extractor as claimed in claim 9 wherein said pump includes a manually operated pump actuator.

11. A bulk extractor as claimed in claim 9 wherein said fluid chamber is defined in part by an inboard cylindrical wall, said inboard wall further defining a sleeve through which passes said coring tube.

12. A bulk extractor as claimed in claim 11 wherein said coring tube is elongated and has opposing ends movably extendable beyond said housing.

13. A bulk extractor as claimed in claim 12 wherein said push piece is elongated and has opposing ends movably extendable beyond said coring tube.

14. A bulk extractor as claimed in claim 13 wherein one of push piece ends includes an extraction remote end having indicia thereon to provide an indication of the depth said coring tube has entered said extraction site.

15. A bulk extractor as claimed in claim 14 wherein said housing is an elongated cylinder and said output port is defined by a handle section extending normal to said elongated housing.

16. A bulk extractor as claimed in claim 5 wherein said hood is rigid and is removably attached to said housing and is transparent.

17. A method for extracting an asbestos bulk sample under substantially continuous negative pressure relative to the ambient atmospheric pressure comprising the steps of:

establishing and maintaining a substantially continuous negative pressure in an extraction region about an extraction site;

manually boring and obtaining a core of said asbestos bulk sample at said extraction site;

withdrawing said sample core from said extraction site;

wetting said extraction site after the step of withdrawing;

depositing said sample core into a container;

wherein the steps of boring, withdrawing and wetting all occur substantially under said substantially continuous negative pressure.

18. A method as claimed in claim 7 wherein the steps of withdrawing and depositing are manually conducted.

19. A method as claimed in claim 7 including the step of viewing said extraction site during the step of manually boring and obtaining the sample core.

20. A method as claimed in claim 7 wherein the step of manually boring includes the step of rotatably sawing to obtain said sample core.

21. A method as claimed in claim 7 wherein a negative pressure is established about said container during the step of depositing.

* * * * *